United States Patent [19]

Devergne et al.

[11] Patent Number: 5,830,451
[45] Date of Patent: Nov. 3, 1998

[54] HAEMATOPOIETIC CYTOKINE EPSTEIN BARR VIRUS-INDUCED PROTEIN

[75] Inventors: Odile Devergne; Elliott D. Kieff, both of Brookline, Mass.

[73] Assignee: Brigham & Women's Hospital, Inc., Boston, Mass.

[21] Appl. No.: 684,687

[22] Filed: Jul. 19, 1996

Related U.S. Application Data

[60] Provisional application No. 60/005,092, Oct. 11, 1995.

[51] Int. Cl.$^6$ .............................. A61K 38/19; C07K 14/52
[52] U.S. Cl. ........................ 424/85.1; 530/351; 435/69.7; 435/71.2; 435/172.3; 435/325; 435/252.3; 435/320.1; 536/23.4; 536/23.5; 536/24.31
[58] Field of Search ..................................... 530/351, 350; 514/2, 8, 12; 424/85.1; 435/69.5, 69.7, 71.2, 172.3, 325, 252.3, 320.1; 536/23.4, 23.5, 24.31

[56] References Cited

PUBLICATIONS

Devergne et al. (1996) J. of Virology vol. 20, No. 2, pp. 1143–1153.
Gubler et al., Proc. Natl. Acad. Sci. USA 88: 4143–4147, 1991.
Zarlenga et al., 12, Biochimica et Biophysica Acta. 1270: 215–217, 1995.
Villinger et al., J. Immunol. 155: 3946–3954, 1995.
Schoenhaut et al., J. Immunol. 148: 3433–3440, 1992.
Wolf et al., J. Immunol. 146; 3074–3081, 1991.
Bazan. Proc. Natl. Acad. Sci. (USA) 87:6934, 1990.
Cosman, Cytokine 5:95, 1993.
Birkenbach et al.,J. Virol. 67:2209–2220, 1993.
D'Andrea et al., J. Exp. Med. 176:1387, 1992.
D'Andrea et al., J. Exp. Med. 178:1041, 1993.

Primary Examiner—Stephen Walsh
Assistant Examiner—Prema Mertz
Attorney, Agent, or Firm—Wolf, Greenfield & Sacks, P.C.

[57] ABSTRACT

A novel heterodimeric haematopoietic cytokine formed from the Epstein Barr Virus-Induced protein 3 (EBI3) and the p35 subunit of Interleukin-12 (IL12) is disclosed. Substantially pure preparations of this EBI3/p35 cytokine, and antibodies thereto, are provided. In addition, isolated nucleic acids encoding the EBI3/p35 cytokine, and recombinant host cells transformed with these nucleic acids, are also provided. Methods of treating patients, using the EBI3/p35 cytokine or nucleic acids encoding the cytokine, are disclosed. The invention also provides for diagnostic assays for detecting pregnancy or threatened spontaneous abortion using antibodies to the cytokine.

9 Claims, 5 Drawing Sheets

A. Cell lysate

B. Culture sup

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 1161 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO (v i) ORIGINAL SOURCE:
    (A) ORGANISM: HOMO SAPIENS (i x) FEATURE:
    (A) NAME/KEY: CDS
    (B) LOCATION: 14..703

(x i) SEQUENCE DESCRIPTION: SEQ ID NO:1:

| | | | | | | | | | | | | | | | | |
|---|---|---|---|---|---|---|---|---|---|---|---|---|---|---|---|---|
| GAATTCCGCA | GCC | ATG | ACC | CCG | CAG | CTT | CTC | CTG | GCC | CTT | GTC | CTC | TGG | | | 49 |
| | Ala | Met | Thr | Pro | Gln | Leu | Leu | Leu | Ala | Leu | Val | Leu | Trp | | | |
| | | 1 | | | 5 | | | | | | | 10 | | | | |
| GCC | AGC | TGC | CCG | CCC | TGC | AGT | GGA | AGG | AAA | GGG | CCC | CCA | GCA | GCT | CTG | 97 |
| Ala | Ser | Cys | Pro | Pro | Cys | Ser | Gly | Arg | Lys | Gly | Pro | Pro | Ala | Ala | Leu | |
| | | 15 | | | | 20 | | | | | 25 | | | | | |
| ACA | CTG | CCC | CGG | GTG | CAA | TGC | CGA | GCC | TCT | CGG | TAC | CCG | ATC | GCC | GTG | 145 |
| Thr | Leu | Pro | Arg | Val | Gln | Cys | Arg | Ala | Ser | Arg | Tyr | Pro | Ile | Ala | Val | |
| | 30 | | | | | 35 | | | | | 40 | | | | | |
| GAT | TGC | TCC | TGG | ACC | CTG | CCG | CCT | GCT | CCA | AAC | TCC | ACC | AGC | CCC | GTG | 193 |
| Asp | Cys | Ser | Trp | Thr | Leu | Pro | Pro | Ala | Pro | Asn | Ser | Thr | Ser | Pro | Val | |
| 45 | | | | | 50 | | | | | 55 | | | | | 60 | |
| TCC | TTC | ATT | GCC | ACG | TAC | AGG | CTC | GGC | ATG | GCT | GCC | CGG | GGC | CAC | AGC | 241 |
| Ser | Phe | Ile | Ala | Thr | Tyr | Arg | Leu | Gly | Met | Ala | Ala | Arg | Gly | His | Ser | |
| | | | | 65 | | | | | 70 | | | | | 75 | | |
| TGG | CCC | TGC | CTG | CAG | CAG | ACG | CCA | ACG | TCC | ACC | AGC | TGC | ACC | ATC | ACG | 289 |
| Trp | Pro | Cys | Leu | Gln | Gln | Thr | Pro | Thr | Ser | Thr | Ser | Cys | Thr | Ile | Thr | |
| | | | 80 | | | | | 85 | | | | | | 90 | | |
| GAT | GTC | CAG | CTG | TTC | TCC | ATG | GCT | CCC | TAC | GTG | CTC | AAT | GTC | ACC | GCC | 337 |
| Asp | Val | Gln | Leu | Phe | Ser | Met | Ala | Pro | Tyr | Val | Leu | Asn | Val | Thr | Ala | |
| | | 95 | | | | | 100 | | | | | 105 | | | | |
| GTC | CAC | CCC | TGG | GGC | TCC | AGC | AGC | AGC | TTC | GTG | CCT | TTC | ATA | ACA | GAG | 385 |
| Val | His | Pro | Trp | Gly | Ser | Ser | Ser | Ser | Phe | Val | Pro | Phe | Ile | Thr | Glu | |
| | 110 | | | | | 115 | | | | | 120 | | | | | |
| CAC | ATC | ATC | AAG | CCC | GAC | CCT | CCA | GAA | GGC | GTG | CGC | CTA | AGC | CCC | CTC | 433 |
| His | Ile | Ile | Lys | Pro | Asp | Pro | Pro | Glu | Gly | Val | Arg | Leu | Ser | Pro | Leu | |
| 125 | | | | | 130 | | | | | 135 | | | | | 140 | |
| GCT | GAG | CGC | CAG | CTA | CAG | GTG | CAG | TGG | GAG | CCT | CCC | GGG | TCC | TGG | CCC | 481 |
| Ala | Glu | Arg | Gln | Leu | Gln | Val | Gln | Trp | Glu | Pro | Pro | Gly | Ser | Trp | Pro | |
| | | | | 145 | | | | | 150 | | | | | 155 | | |
| TTC | CCA | GAG | ATC | TTC | TCA | CTG | AAG | TAC | TGG | ATC | CGT | TAC | AAG | CGT | CAG | 529 |
| Phe | Pro | Glu | Ile | Phe | Ser | Leu | Lys | Tyr | Trp | Ile | Arg | Tyr | Lys | Arg | Gln | |
| | | | 160 | | | | | 165 | | | | | 170 | | | |
| GGA | GCT | GCG | CGC | TTC | CAC | CGG | GTG | GGG | CCC | ATT | GAA | GCC | ACG | TCC | TTC | 577 |
| Gly | Ala | Ala | Arg | Phe | His | Arg | Val | Gly | Pro | Ile | Glu | Ala | Thr | Ser | Phe | |
| | | 175 | | | | | 180 | | | | | 185 | | | | |
| ATC | CTC | AGG | GCT | GTG | CGG | CCC | CGA | GCC | AGG | TAC | TAC | GTC | CAA | GTG | GCG | 625 |
| Ile | Leu | Arg | Ala | Val | Arg | Pro | Arg | Ala | Arg | Tyr | Tyr | Val | Gln | Val | Ala | |
| | 190 | | | | | 195 | | | | | 200 | | | | | |
| GCT | CAG | GAC | CTC | ACA | GAC | TAC | GGG | GAA | CTG | AGT | GAC | TGG | AGT | CTC | CCC | 673 |
| Ala | Gln | Asp | Leu | Thr | Asp | Tyr | Gly | Glu | Leu | Ser | Asp | Trp | Ser | Leu | Pro | |
| 205 | | | | | 210 | | | | | 215 | | | | | 220 | |
| GCC | ACT | GCC | ACA | ATG | AGC | CTG | GGC | AAG | TAGCAAGGGC | TTCCCGCTGC | | | | | | 720 |
| Ala | Thr | Ala | Thr | Met | Ser | Leu | Gly | Lys | | | | | | | | |
| | | | | 225 | | | | | 230 | | | | | | | |
| CTCCAGACAG | CACCTGGGTC | CTCGCCACCC | TAAGCCCCGG | GACACCTGTT | GGAGGGCGGA | 780 |
| TGGGATCTGC | CTAGCCTGGG | CTGGAGTCCT | TGCTTTGCTG | CTGCTGAGCT | GCCGGGCAAC | 840 |
| CTCAGATGAC | CGACTTTTCC | CTTTGAGCCT | CAGTTTCTCT | AGCTGAGAAA | TGGAGATGTA | 900 |
| CTACTCTCTC | CTTTACCTTT | ACCTTTACCA | CAGTGCAGGG | CTGACTGAAC | TGTCACTGTG | 960 |
| AGATATTTTT | TATTGTTTAA | TTAGAAAAGA | ATTGTTGTTG | GGCTGGGCGC | AGTGGATCGC | 1020 |

| | | | | | | |
|---|---|---|---|---|---|---|
| ACCTGTAATC | CCAGTCACTG | GGAAGCCGAC | GTGGGTGGGT | AGCTTGAGGC | CAGGAGCTCG | 1080 |
| AAACCAGTCC | GGGCCACACA | GCAAGACCCC | ATCTCTAAAA | AATTAATATA | AATATAAAAT | 1140 |
| AAAAAAAAAA | AAAAGGAATT | C | | | | 1161 |

( 2 ) INFORMATION FOR SEQ ID NO:2:

( i ) SEQUENCE CHARACTERISTICS:
        ( A ) LENGTH: 229 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Thr  Pro  Gln  Leu  Leu  Leu  Ala  Leu  Val  Leu  Trp  Ala  Ser  Cys  Pro
  1              5                        10                        15
Pro  Cys  Ser  Gly  Arg  Lys  Gly  Pro  Pro  Ala  Ala  Leu  Thr  Leu  Pro  Arg
               20                        25                        30
Val  Gln  Cys  Arg  Ala  Ser  Arg  Tyr  Pro  Ile  Ala  Val  Asp  Cys  Ser  Trp
               35                        40                        45
Thr  Leu  Pro  Pro  Ala  Pro  Asn  Ser  Thr  Ser  Pro  Val  Ser  Phe  Ile  Ala
          50                        55                        60
Thr  Tyr  Arg  Leu  Gly  Met  Ala  Ala  Arg  Gly  His  Ser  Trp  Pro  Cys  Leu
 65                        70                        75                        80
Gln  Gln  Thr  Pro  Thr  Ser  Thr  Ser  Cys  Thr  Ile  Thr  Asp  Val  Gln  Leu
                    85                        90                        95
Phe  Ser  Met  Ala  Pro  Tyr  Val  Leu  Asn  Val  Thr  Ala  Val  His  Pro  Trp
               100                       105                       110
Gly  Ser  Ser  Ser  Ser  Phe  Val  Pro  Phe  Ile  Thr  Glu  His  Ile  Ile  Lys
               115                       120                       125
Pro  Asp  Pro  Pro  Glu  Gly  Val  Arg  Leu  Ser  Pro  Leu  Ala  Glu  Arg  Gln
          130                       135                       140
Leu  Gln  Val  Gln  Trp  Glu  Pro  Pro  Gly  Ser  Trp  Pro  Phe  Pro  Glu  Ile
145                       150                       155                       160
Phe  Ser  Leu  Lys  Tyr  Trp  Ile  Arg  Tyr  Lys  Arg  Gln  Gly  Ala  Ala  Arg
               165                       170                       175
Phe  His  Arg  Val  Gly  Pro  Ile  Glu  Ala  Thr  Ser  Phe  Ile  Leu  Arg  Ala
               180                       185                       190
Val  Arg  Pro  Arg  Ala  Arg  Tyr  Tyr  Val  Gln  Val  Ala  Ala  Gln  Asp  Leu
               195                       200                       205
Thr  Asp  Tyr  Gly  Glu  Leu  Ser  Asp  Trp  Ser  Leu  Pro  Ala  Thr  Ala  Thr
     210                       215                       220
Met  Ser  Leu  Gly  Lys
225
```

( 2 ) INFORMATION FOR SEQ ID NO:3:

( i ) SEQUENCE CHARACTERISTICS:
        ( A ) LENGTH: 1316 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: HOMO SAPIENS ( i x ) FEATURE:
    ( A ) NAME/KEY: CDS
    ( B ) LOCATION: 102..863

( x i ) SEQUENCE DESCRIPTION: SEQ ID NO:3:

```
GGTCACCGAG AAGCTGATGT AGAGAGAGAC ACAGAAGGAG ACAGAAAGCA AGAGACCAGA            60

GTCCCGGGAA AGTCCTGCCG CGCCTCGGGA CAATTATAAA A ATG TGG CCC CCT              113
                                              Met Trp Pro Pro
                                                1

GGG TCA GCC TCC CAG CCA CCG CCC TCA CCT GCC GCG GCC ACA GGT CTG             161
Gly Ser Ala Ser Gln Pro Pro Pro Ser Pro Ala Ala Ala Thr Gly Leu
  5              10                  15                      20

CAT CCA GCG GCT CGC CCT GTG TCC CTG CAG TGC CGG CTC AGC ATG TGT             209
His Pro Ala Ala Arg Pro Val Ser Leu Gln Cys Arg Leu Ser Met Cys
                 25                  30                      35

CCA GCG CGC AGC CTC CTC CTT GTC GCT ACC CTG GTC CTC CTG GAC CAC             257
Pro Ala Arg Ser Leu Leu Leu Val Ala Thr Leu Val Leu Leu Asp His
             40                  45                      50

CTC AGT TTG GCC AGA AAC CTC CCC GTG GCC ACT CCA GAC CCA GGA ATG             305
Leu Ser Leu Ala Arg Asn Leu Pro Val Ala Thr Pro Asp Pro Gly Met
         55                  60                  65

TTC CCA TGC CTT CAC CAC TCC CAA AAC CTG CTG AGG GCC GTC AGC AAC             353
Phe Pro Cys Leu His His Ser Gln Asn Leu Leu Arg Ala Val Ser Asn
     70                  75                  80

ATG CTC CAG AAG GCC AGA CAA ACT CTA GAA TTT TAC CCT TGC ACT TCT             401
Met Leu Gln Lys Ala Arg Gln Thr Leu Glu Phe Tyr Pro Cys Thr Ser
 85                  90                  95                 100

GAA GAG ATT GAT CAT GAA GAT ATC ACA AAA GAT AAA ACC AGC ACA GTG             449
Glu Glu Ile Asp His Glu Asp Ile Thr Lys Asp Lys Thr Ser Thr Val
                105                 110                 115

GAG GCC TGT TTA CCA TTG GAA TTA ACC AAG AAT GAG AGT TGC CTA AAT             497
Glu Ala Cys Leu Pro Leu Glu Leu Thr Lys Asn Glu Ser Cys Leu Asn
            120                 125                 130

TCC AGA GAG ACC TCT TTC ATA ACT AAT GGG AGT TGC CTG GCC TCC AGA             545
Ser Arg Glu Thr Ser Phe Ile Thr Asn Gly Ser Cys Leu Ala Ser Arg
        135                 140                 145

AAG ACC TCT TTT ATG ATG GCC CTG TGC CTT AGT AGT ATT TAT GAA GAC             593
Lys Thr Ser Phe Met Met Ala Leu Cys Leu Ser Ser Ile Tyr Glu Asp
    150                 155                 160

TTG AAG ATG TAC CAG GTG GAG TTC AAG ACC ATG AAT GCA AAG CTT CTG             641
Leu Lys Met Tyr Gln Val Glu Phe Lys Thr Met Asn Ala Lys Leu Leu
165                 170                 175                 180

ATG GAT CCT AAG AGG CAG ATC TTT CTA GAT CAA AAC ATG CTG GCA GTT             689
Met Asp Pro Lys Arg Gln Ile Phe Leu Asp Gln Asn Met Leu Ala Val
                185                 190                 195

ATT GAT GAG CTG ATG CAG GCC CTG AAT TTC AAC AGT GAG ACT GTG CCA             737
Ile Asp Glu Leu Met Gln Ala Leu Asn Phe Asn Ser Glu Thr Val Pro
            200                 205                 210

CAA AAA TCC TCC CTT GAA GAA CCG GAT TTT TAT AAA ACT AAA ATC AAG             785
Gln Lys Ser Ser Leu Glu Glu Pro Asp Phe Tyr Lys Thr Lys Ile Lys
        215                 220                 225

CTC TGC ATA CTT CTT CAT GCT TTC AGA ATT CGG GCA GTG ACT ATT GAT             833
Leu Cys Ile Leu Leu His Ala Phe Arg Ile Arg Ala Val Thr Ile Asp
    230                 235                 240

AGA GTG ATG AGC TAT CTG AAT GCT TCC TAAAAAGCGA GGTCCCTCCA                   880
Arg Val Met Ser Tyr Leu Asn Ala Ser
245                 250

AACCGTTGTC ATTTTTATAA AACTTTGAAA TGAGGAAACT TTGATAGGAT GTGGATTAAG           940

AACTAGGGAG GGGGAAAGAA GGATGGGACT ATTACATCCA CATGATACCT CTGATCAAGT          1000
```

-continued

| | | | | | |
|---|---|---|---|---|---|
| ATTTTTGACA | TTTACTGTGG | ATAAATTGTT | TTTAAGTTTT | CATGAATGAA | TTGCTAAGAA | 1060 |
| GGGAAAATAT | CCATCCTGAA | GGTGTTTTTC | ATTCACTTTA | ATAGAAGGGC | AAATATTTAT | 1120 |
| AAGCTATTTC | TGTACCAAAG | TGTTTGTGGA | AACAAACATG | TAAGCATAAC | TTATTTTAAA | 1180 |
| ATATTTATTT | ATATAACTTG | GTAATCATGA | AAGCATCTGA | GCTAACTTAT | ATTTATTTAT | 1240 |
| GTTATATTTA | TTAAATTATT | TATCAAGTGT | ATTTGAAAAA | TATTTTAAG | TGTTCTAAAA | 1300 |
| ATAAAGTAT | TGAATT | | | | | 1316 |

( 2 ) INFORMATION FOR SEQ ID NO:4:

( i ) SEQUENCE CHARACTERISTICS:
        ( A ) LENGTH: 253 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Trp Pro Pro Gly Ser Ala Ser Gln Pro Pro Ser Pro Ala Ala
 1           5                  10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
            35                  40                  45

Leu Leu Asp His Leu Ser Leu Ala Arg Asn Leu Pro Val Ala Thr Pro
            50                  55                  60

Asp Pro Gly Met Phe Pro Cys Leu His His Ser Gln Asn Leu Leu Arg
 65                  70                  75                  80

Ala Val Ser Asn Met Leu Gln Lys Ala Arg Gln Thr Leu Glu Phe Tyr
                    85                  90                  95

Pro Cys Thr Ser Glu Glu Ile Asp His Glu Asp Ile Thr Lys Asp Lys
                100                 105                 110

Thr Ser Thr Val Glu Ala Cys Leu Pro Leu Glu Leu Thr Lys Asn Glu
            115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
                180                 185                 190

Met Leu Ala Val Ile Asp Glu Leu Met Gln Ala Leu Asn Phe Asn Ser
            195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single (D) TOPOLOGY: linear (ii) MOLECULE TYPE: peptide (iii) HYPOTHETICAL: NO (vi) ORIGINAL SOURCE:
    (A) ORGANISM: HOMO SAPIENS (ix) FEATURE:
    (A) NAME/KEY: Modified-site
    (B) LOCATION: 1..6
    (D) OTHER INFORMATION: /label=KINASE_SITE (xi) SEQUENCE DESCRIPTION: SEQ ID NO:5:

```
Arg  Arg  Ala  Ser  Val  Gly
 1                    5
```

(2) INFORMATION FOR SEQ ID NO:6:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (iii) HYPOTHETICAL: NO (vi) ORIGINAL SOURCE:
    (A) ORGANISM: HOMO SAPIENS (ix) FEATURE:
    (A) NAME/KEY: Binding-site
    (B) LOCATION: 1..8
    (D) OTHER INFORMATION: /label=FLAG_EPITOPE (xi) SEQUENCE DESCRIPTION: SEQ ID NO:6:

```
Asp  Tyr  Lys  Asp  Asp  Asp  Asp  Lys
 1                    5
```

(2) INFORMATION FOR SEQ ID NO:7:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (iii) HYPOTHETICAL: NO (vi) ORIGINAL SOURCE:
    (A) ORGANISM: HOMO SAPIENS (ix) FEATURE:
    (A) NAME/KEY: Region
    (B) LOCATION: 1..5
    (D) OTHER INFORMATION: /note= "SIMILAR TO HAEMATOPOIETIN
        RECEPTOR FAMILY CONSENSUS SEQUENCE"

(xi) SEQUENCE DESCRIPTION: SEQ ID NO:7:

```
Leu  Ser  Asp  Trp  Ser
 1                    5
```

(2) INFORMATION FOR SEQ ID NO:8:

(i) SEQUENCE CHARACTERISTICS:
    (A) LENGTH: 5 amino acids
    (B) TYPE: amino acid
    (C) STRANDEDNESS: single
    (D) TOPOLOGY: linear

```
( i i ) MOLECULE TYPE: peptide ( i i i ) HYPOTHETICAL: YES ( v i ) ORIGINAL SOURCE:
        ( A ) ORGANISM: HOMO SAPIENS ( i x ) FEATURE:
        ( A ) NAME/KEY: Region
        ( B ) LOCATION: 1..5
        ( D ) OTHER INFORMATION: /note= "HAEMATOPOIETIN RECEPTOR
              FAMILY CONSENSUS SEQUENCE"

( x i ) SEQUENCE DESCRIPTION: SEQ ID NO:8:

Trp  Ser  Xaa  Trp  Ser
1                    5
```

HAEMATOPOIETIC CYTOKINE EPSTEIN BARR VIRUS-INDUCED PROTEIN

Research for the present invention was supported in part by grant NCI 5R35 CA47006-09 from the National Institutes of Health of the United States. The U.S. government retains certain rights in the invention.

RELATED APPLICATIONS

This invention claims priority from a provisional application, U.S. Ser. No.60/005,092, filed Oct. 11, 1995.

FIELD OF THE INVENTION

The present invention relates to the fields of immunology and cytokines. The present invention provides a novel purified complex, EBI3/p35, and further provides nucleic acids encoding this novel complex. The EBI3/p35 complex, and nucleic acids operably encoding it, may be formulated in pharmaceutical compositions and used in the treatment of various conditions. In addition, antibodies to EBI3/p35 may be used in diagnostic tests.

BACKGROUND OF THE INVENTION

Interleukin-12 (IL12) is a 70-kDa heterodimeric cytokine composed of two disulfide-linked glycosylated chains, p40 and p35. The p35 subunit is structurally related to other alpha-helix rich haematopoietin cytokines, while the p40 subunit is a member of the haematopoietin receptor family. IL 12 was originally identified and purified from the culture cell supernatant of Epstein-Barr virus (EBV) transformed B lymphoblastoid cell lines, based on its ability to stimulate the maturation of cytotoxic lymphocytes (Cytotoxic Lymphocyte Maturation Factor) and the cytotoxicity of NK cells (Natural Killer cell Stimulatory Factor). IL12 has pleiotropic effects on T and NK cells including: (i) induction of IFN-γ production; (ii) proliferation; and (iii) enhancement of cytotoxic activity. More recently, IL12 was shown to play a major role in the regulation of immune responses, by promoting the development of T helper type 1 (Th 1) responses, while inhibiting the development of Th2 cells (reviewed in Trichieri, (1993) *Immunol. Today* 14:335). Effects of IL12 on B lymphocyte differentiation (Jelinek et al., (1995) *J. Immunol.* 154:1606) and on human haematopoiesis (Bellone et al., (1994) *J. Immunol.* 153:930) have also been reported.

IL12 is mainly produced by macrophages and other accessory cells (D'Andrea et al., (1992) *J. Exp. Med.* 176:1387). Human keratinocytes and keratinocyte cell lines have also been reported to express IL12 (Aragane et al., (1994) *J. Immunol.* 153:5366). All IL12 expressing cell types analyzed so far produce the biologically active p70 heterodimer, together with a large excess of the free p40 subunit. No production of free p35 has been reported. Expression of p35 appears to be ubiquitous and minimally regulated, whereas p40 expression is restricted to cell lines expressing the IL12 heterodimer and is inducible (D'Andrea et al., (1992) *J. Exp. Med.* 176:1387; D'Andrea et al., (1993) *J. Exp. Med.* 178:1041).

IL12 binding sites of three different affinities have been identified on activated T cells, suggesting that the IL12 receptor (IL12R) is composed of several subunits (Chua et al., (1994) *J. Immunol.* 153:128). Only one chain encoding a 100 kDa low affinity IL12R component has been cloned (Chua et al., (1994) *J. Immunol.* 153:128). This IL12 receptor subunit is a member of the haematopoietin receptor family, homologous to gp130. In addition to IL12, homodimers of the p40 subunit can also bind the IL12R, and act in vitro as an antagonist for the IL12 heterodimer (Ling et al., (1995) *J. Immunol.* 154:116). However, there is no evidence that p40 homodimers exist in vivo.

SUMMARY OF THE INVENTION

The invention involves the discovery that EBI3, an Epstein Barr Virus induced protein, forms a heterodimer with the IL12 p35 subunit in vivo. This complex has the ability to modulate the immune response and to influence the activity of cells, including hematopoietic, embryonal and neural cells. It therefore is believed useful in connection with treating a variety of conditions, including allergy, autoimmunity, host versus graft rejection, infectious disease, etc. EBI3 is present in large quantities in placental syncytial trophoblasts, and thus it is also believed that the complex can be used to down regulate the maternal fetal immune response, decreasing the likelihood of spontaneous abortion. It further can be used to raise antibodies, which antibodies can be used inter alia, to isolate the complex, to identify tissues expressing the complex (including recombinant cells) and to diagnose pregnancy.

According to one aspect of the invention, there is provident substantially pure EBI3/p35 protein complex. The EBI3/p35 protein complex comprises a heterodimer of a p35 subunit of IL12 and an EBI3 protein. In one preferred embodiment the EBI3 protein has the amino acid sequence disclosed as SEQ ID NO: 2. In other embodiments, the EBI3 protein is an allelomorph of the sequence disclosed as SEQ ID NO: 2. In another preferred embodiment, the p35 subunit includes the amino acid sequence disclosed as SEQ ID NO: 4. In other embodiments, the p35 subunit may be an allelomorph of the sequence disclosed as SEQ ID NO: 4.

According to another aspect of the invention, pharmaceutical preparations are provided. The pharmaceutical preparations include substantially pure EBI3/p35 complex as described above, together with a pharmaceutically acceptable carrier. Such preparations preferably are sterile.

According to another aspect of the invention, there are provided isolated nucleic acids comprising an expression vector including a first expression cassette and a second expression cassette in which the first cassette operably encodes a p35 subunit of IL12 and the second expression cassette operably encodes an EBI3 protein. In preferred embodiments, the second expression cassette includes (a) the complete coding region of SEQ ID NO: 1; (b) sequences which hybridize under stringent hybridization conditions to SEQ ID NO: 1, or its complement, and which code for EBI3 protein; or (c) sequences which differ from (a) and (b) in codon sequence due to the degeneracy of the genetic code. The first expression cassette likewise can include (a) the complete coding region of SEQ ID NO: 3; sequences which hybridize under stringent hybridization conditions to the coding region of SEQ ID NO: 3, or its complement, and which code for p35 subunit; or (c) sequences which differ from (a) and (b) in codon sequence due to the degeneracy of the genetic code.

Substantially pure polypeptide complexes coded for by the foregoing isolated nucleic acids also are embraced by the invention.

The present invention also provides recombinant host cells including any of the above-described isolated nucleic acids which encode an EBI3/p35 cytokine. It is a further object to the invention to provide recombinant host cells which include two separate nucleic acids, one of which operably encodes an EBI3 protein and one of which operably encodes the IL12 p35 subunit. Expression of such nucleic acids in a recombinant host cell allows production of the EBI3/p35 heterodimer.

The invention also embraces not only substantially pure EBI3/p35, but also functional variants and fragments which are heterodimers as well as fusion proteins wherein the heterodimer or fragment thereof is manufactured as covalently attached EBI3-p35, or fragments thereof including at least a portion of EBI3 and a portion of p35 which form an active complex.

It is a particular object of the present invention to provide a method of diagnosing pregnancy and threatened spontaneous abortion comprising obtaining a fluid sample such as serum, urine or uterine secretion from a subject suspected of being pregnant; contacting the sample with an antibody to the EBI3/p35 heterodimer; and determining binding of the antibody and EBI3/p35 heterodimer within the sample as a measure of pregnancy.

According to another aspect of the invention, a method for modulating the immune system of a subject is provided. An EBI3/p35 protein complex is administered to a subject in need of such immune modulation in an amount effective to modulate the immune response of the subject. The EBI3/p35 protein complex may be substantially pure protein complex formulated as a pharmaceutical. The EBI3/p35 protein complex also may be expressed in recombinant cells which are placed within the subject. For example, tissue transplants, including organ transplants may be genetically engineered to express EBI3/p35 so as to modulate the immune system of the host and reduce the chances of tissue or organ rejection. The EBI3/p35 protein complex may be any of the embodiments that are described above.

The invention thus contemplates methods for modulating the immune system to achieve particular therapeutic purposes. In one embodiment, the EBI3/p35 protein complex is administered to a pregnant woman or a woman with a history of infertility to reduce the chances of spontaneous abortion. In another embodiment, the EBI3/p35 protein complex is administered to a subject scheduled to have or who has had a tissue transplant, including but not limited to an organ transplant, in order to reduce the likelihood of tissue or organ transplant rejection. In another embodiment, the EBI3/p35 protein complex is administered to a subject that has an autoimmune condition to ameliorate the autoimmune condition. One example is autoimmune disease due to NK or cytotoxic T-cell hyperactivity. In another embodiment, the EBI3/p35 protein complex is administered to a subject who has an infectious disease to ameliorate that condition. One example involves infectious diseases which result in hyperactive cytotoxic T-cell responses that threaten organ destruction. It is even possible to supply a developing embryo or fetus, perhaps transiently, with recombinant nucleic acids encoding the EBI3/p35 protein complex to assist in preventing spontaneous abortion.

According to yet another aspect of the invention, methods for modulating the activity of cells is provided. The cells are contacted with an EBI3/p35 protein complex in an amount sufficient to modulate the growth, differentiation or development of the cells. The cells, for example, can be hematopoietic cells, embryonal cells or neural cells. A protein complex can be supplied in substantially pure form or can be provided by recombinant expression. The invention thus also embraces in vitro uses of the purified and isolated materials of the invention. These in vitro uses include, but are not limited to, making recombinant cells for transplantation into a host, making recombinant cells for expressing and purifying EBI3/p35 protein complex, and contacting cells such as a heterogeneous population of lymphocytes to selectively influence the growth, development, and/or differentiation of particular subsets of cells, such as by arresting cytotoxic T-cell or NK-cell development.

These and other aspects of the invention are described in greater detail below.

DETAILED DESCRIPTION OF THE INVENTION

Definitions

Figure 1:
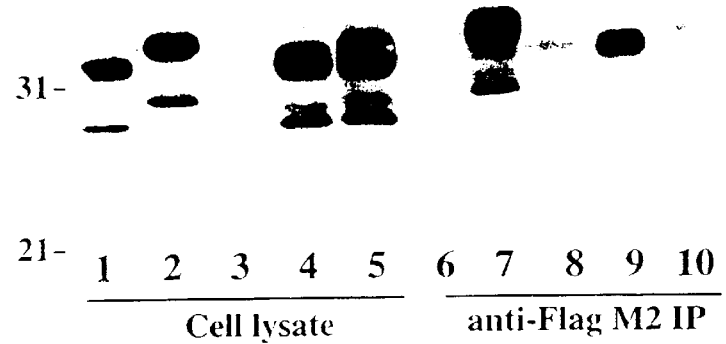
FIG. 1 contains computer digitized images of chemiluminescent immunoblots demonstrating that EBI3 coprecipitates with FLAG-tagged p35 from both the cell lysate (FIG. 1A) or the cell culture supernatant (FIG. 1B) of BJAB cells coexpressing both proteins.
Figure 1:
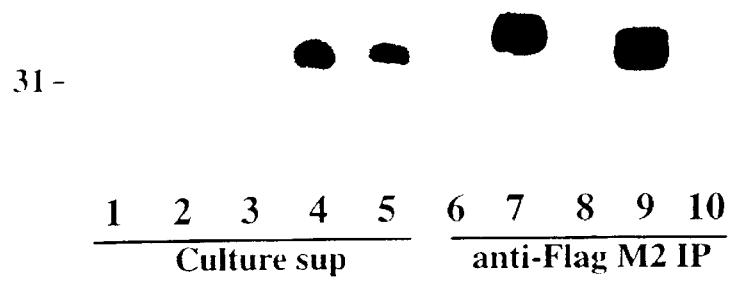

In order to more clearly and concisely describe the subject matter of the present invention, the following definitions are provided for specific terms used in the claims appended hereto:

As used herein, the term "interleukin-12" and the abbreviation "IL12" mean the heterodimeric human haematopoietic cytokine well known in the art and described in the references cited above. IL12 is a 70–75 kDa glycoprotein comprising two disulfide-linked subunits designated p35 and p40. As used herein, the term "IL12 p35 subunit," or simply "p35," means the approximately 35 kDa subunit of IL12 well known in the art and described in the references cited above. An amino acid sequence of one human allele of the IL12 p35 subunit is reported in Wolf, et al. (1991) *J. Immunol.* 146:3074–3081 and is reproduced herein as SEQ ID NO: 4.

As used herein, the abbreviation "EBI3" means the Epstein Barr Virus induced protein number 3 described in the experimental section below. The EBI3 protein has a predicted molecular mass of approximately 25.3 kDa and an apparent molecular mass of approximately 33 kDa and forms a heterodimer with the IL12 p35 subunit. The nucleotide sequence of one human EBI3 allele and the amino acid sequence of the corresponding EBI3 protein are reproduced herein as SEQ ID NO: 1 and SEQ ID NO: 2.

As used herein, the abbreviation "EBI3/p35" means the heterodimer formed by the EBI3 protein and the IL12 p35 subunit.

As used herein with respect to polypeptides, the term "substantially pure" means that the polypeptides are essentially free of other substances with which they may be found in natural or in vivo systems to an extent practical and appropriate for their intended use. In particular, the polypeptides are sufficiently pure and are sufficiently free from other biological constituents of their hosts cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a small percentage by weight of the preparation. The polypeptide is nonetheless substantially pure in that it has been substantially separated from the substances with which it may be associated in living systems.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined Gene. Promoters may be constitutive or inducible. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, the term "stringent conditions" refers to parameters known to those skilled in the art. One example of stringent conditions is hybridization at 65° C. in hybridization buffer (3.5×SSC, 0.02% Ficoll, 0.02% polyvinyl pyrolidone, 0.02% bovine serum albumin (BSA), 25 mM $NaH_2PO_4$ (pH7), 0.5% SDS, 2 mM EDTA). SSC is 0.15M sodium chloride/0.15M sodium citrate, pH7; SDS is sodium dodecylsulphate; and EDTA is ethylene diamine tetra acetic acid. There are other conditions, reagents, and so forth which can be used, which result in the same degree of stringency. A skilled artisan will be familiar with such conditions, and thus they are not given here. The skilled artisan also is familiar with the methodology for screening cells for expression of such molecules, which then are routinely isolated, followed by isolation of the pertinent nucleic acid. Thus, homologs and alleles of EBI3 proteins and p35 subunits, as well as nucleic acids encoding the same, may be obtained routinely, and the invention is not intended to be limited to the specific sequences disclosed.

As used herein, a "therapeutically effective amount" of the cytokines or nucleic acids of the invention is a dosage large enough to produce the desired effect on the activity and/or proliferation of cells. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the condition being treated, and can be determined by one of skill in the art. The dosage may be adjusted by the individual physician or veterinarian in the event of any complication.

As used herein, subject means humans, nonhuman primates, dogs, cats, sheep, horses, cows, pigs, goats, and rodents.

EBI3/p35: A Novel Cytokine

It is one object of the present invention to provide substantially pure preparations of novel complex comprising a heterodimer of the p35 subunit of interleukin-12 and the EBI3 protein. This novel heterodimer is referred to as EBI3/p35.

Our data indicate that the p35 subunit of IL12 can associate with EBI3, a novel soluble cytokine receptor homologous to IL12 p40. EBI3 was originally identified in and cloned from an EBV- infected Burkitt lymphoma cell cDNA library. EBI3 was noted to have 27% identity to the IL12 p40 subunit and has conservative substitutions at many other residues. EBI3 further resembles IL12 p40 in that both genes have a 3' untranslated Alu repeat sequence. Also similarly to IL12 p40 and in contrast to all other members of the haematopoietin receptor family, EBI3 lacks a membrane anchoring motif and is predicted to be secreted. EBI3 is turned on in EBV-transformed B lymphocytes which must escape from NK and CD8 cytotoxic T cell destruction and is expressed at even higher levels in human placental syncytiotrophoblasts.

We recently observed that these two subunits (EBI3 and IL12 p35), when coexpressed in the same cell form a new soluble heteromeric cytokine, which we now designate EBI3/p35. EBI3 was not well secreted from cells when over expressed alone in B lymphoblasts, and tended to accumulate in the endoplasmic reticulum associated with a molecular chaperone, calnexin, suggesting that there was a natural partner that was not present in high amounts in these cells. Similarly, p35 is not secreted efficiently in the absence of a partner. However, coexpression of EBI3 and IL12 p35 in the same cell results in enhanced p35 secretion (higher ratio of secreted as compared to intracellular p35 when EBI3 is coexpressed). P35 coexpression had a reciprocal effect on EBI3 biosynthesis. These data indicate that EBI3 is a natural partner for p35. Based on the effects of EBI3 and p35 coexpression on their secretion, the formation of heteromeric molecules in the supernatants of cotransfected cells, the evidence that p35 is expressed in most cells, and the evidence that EBI3 is expressed in syncytial trophoblasts and at lower levels in some activated lymphocytes, we conclude that EBI3/p35 is naturally secreted from syncytial trophoblasts and some activated lymphocytes as a natural human cytokine.

Based on the findings that EBI3 expression is turned on by EBV in latently infected cells which need to antagonize the effects of IL12 in increasing anti-EBV-infected cell cytotoxicity, and is naturally expressed at even higher levels in the placenta which needs to protect itself and the developing fetus from IL12 regulated NK and CD8 cytotoxic T cell activity, it appeared possible that the EBI3/p35 heterodimer functions as a modulator of IL12 activities. This suggestion is also supported by the fact that, in the natural cytokine EBI3/p35, more than 60% of the heteromeric protein is identical to IL12. In addition to having an effect on IL12 activity, EBI3 could modulate IL12 biosynthesis. Indeed, by associating with the p35 subunit, EBI3 could prevent p35 from associating with p40 in cells expressing both proteins. At present, no data showing direct IL12 antagonist activity are available; EBI3/p35 does not affect IL12 induced cell DNA synthesis or interferon release in human peripheral blood mononuclear cell assays and it does not bind to the previously identified IL12 receptors. EBI3, however, is made in large quantities by syncytial trophoblasts, and these cells are the most proximal fetal cells to the maternal circulation, likely down regulating the maternal fetal immune response. EBI3/p35 complex, thus, is still believed to act as a down regulator of cell-mediated NK and/or CD8 cytotoxicity and/or of Th1 responses, therefore favoring fetal implantation or expansion of virus-infected cells.

The amino acid sequence of one human allelomorph of the EBI3 protein is reproduced herein as SEQ ID NO: 2. As will be obvious to one of ordinary skill in the art, functional allelomorphic variants of this EBI3 protein may exist in the human population and may be used in accordance with the present invention. Such allelomorphic variants are obvious equivalents of the EBI3 protein described by SEQ ID NO: 2. In addition, one of ordinary skill in the art may, without undue experimentation, produce variants of the EBI3 protein which are equivalent to the protein of SEQ ID NO: 2 by making, for example, conservative substitutions of one or more amino acids. Conservative substitutions include the replacement of an amino acid residue by another, chemically and biologically similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. In addition, the first 20 amino acids of the EBI3 protein are highly hydrophobic and are predicted to be a cleavable signal peptide. Thus, variants of the EBI3 protein in which all or some of the amino acids, including all or some of the first 20 amino acids, are omitted would be equivalents of the complete protein.

The amino acid sequence of one human allelomorph of the IL12 p35 subunit protein is reproduced herein as SEQ ID NO: 4. This sequence is available in GenBank under accession number M65291 and was first reported in Wolf, et al. (1991) *J. Immunol.* 146:3074–3081. As will be obvious to one of ordinary skill in the art, functional allelomorphic variants of the p35 protein may exist in the human population and may be used in accordance with the present invention. Such allelomorphic variants are obvious equivalents of the p35 protein described by SEQ ID NO: 4. In addition, one of ordinary skill in the art may, without undue experimentation, produce variants of the IL12 p35 subunit which are equivalent to the protein of SEQ ID NO: 4 by making, for example, conservative substitutions of one or more amino acids. Conservative substitutions include the replacement of an amino acid residue by another, chemically and biologically similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. As is clear from SEQ ID NO.:3, the nucleotide sequence of the IL12 gene has two potential start codons (ATG) which are in-frame with each other. SEQ ID NO: 3 assumes that the first ATG sequence is the actual start codon. The second ATG, 102 bp downstream of the first, encodes the Met residue labeled as position 35 in SEQ ID NO: 3. This second ATG may be the actual start codon. The N-terminal residues of the IL12 p35 subunit appear to be a signal peptide and the mature peptide is believed to begin approximately at the residue numbered 57 in SEQ ID NO: 3 and SEQ ID NO: 4. Variants of the p35 protein in which all or part of the signal peptide is omitted would be equivalents of the complete protein. Functional portions of any of the foregoing also are embraced by the invention.

EBI3 and p35 also can be produced as a fusion protein. As will be known to one of ordinary skill in the art, the two polypeptides can be fused by insertion of a short, flexible linker which permits sufficient rotational freedom of the polypeptides such that protein function is not hindered.

Substantially pure EBI3/p35 can be obtained from host cells expressing the cytokine by standard methods of protein purification which are well known in the art. Such host cells may be produced using the isolated nucleic acids of the present invention described below.

Nucleic Acids Encoding EBI3/p35 and Expression Thereof

It is another object of the present invention to provide isolated nucleic acids, and in particular, expression vectors, encoding the peptides of EBI3/p35. Clearly, the nucleic acids encoding the EBI3 and IL12 p35 subunit may be separate molecules or vectors but, more preferably, both polypeptides are encoded by a single nucleic acid molecule or vector such that the single vector can transform or transfect a host cell and lead to expression of EBI3/p35. That is, a DNA expression vector for expressing the heterodimeric EBI3/p35 provides a system for independently cloning (inserting) the two translatable DNA sequences into two separate cassettes present in the vector, to form two separate cistrons for expressing the first and second polypeptides of the heterodimeric cytokine. The DNA expression vector for expressing two cistrons is referred to as a dicistronic expression vector.

Preferably, the dicistronic expression vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first EBI3/p35 polypeptide component that is produced when an insert translatable DNA sequence (insert DNA) is directionally inserted into the cassette via the sequence of nucleotides adapted for directional ligation.

The dicistronic expression vector also contains a second cassette for expressing the second EBI3/p35 polypeptide component. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second EBI3/p35 polypeptide component comprising a secretion signal with a polypeptide coded by the insert DNA.

Optionally, the EBI3 and p35 polypeptides are encoded by a single nucleic acid which encodes a fusion protein, as described above, operably joined to a single set of upstream and downstream regulatory sequences. The coding regions for EBI3 and p35 are preferably joined by a short oligonucleotide sequence which encodes a short and flexible peptide linker between the EBI3 and p35 polypeptides. The construction of linkeers of various lengths, flexibility, and conformation is well known to those of ordinary skill in the art. The oligonucleotide encoding the peptide linker, of course, is selected to maintain the translation reading frame of the portion of the nucleic acid located downstream of the oligonucleotide. The construction of a nucleic acid encoding a functional fusion protein including the EBI3 and p35 proteins will be known to one of ordinary skill in the art and may be accomplished without undue experimentation.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAM-neo, pKRC and the like. Preferably, the selected vector of the present invention has the capacity to autonomously replicate in the selected host cell. Useful prokaryotic hosts include bacteria such as *E. coli, Bacillus, Streptomyces, Pseudomonas, Salmonella, Serratia*, and the like.

To express EBI3/p35 in a prokaryotic cell, it is necessary to operably join the EBI3 sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the β-amylase (Ulmanen et al., *J. Bacteriol.* 162:176–182 (1985)) and the ζ-28-specific promoters of *B. subtilis* (Gilman et al., *Gene sequence* 32:11–20 (1984)), the promoters of the bacteriophages of *Bacillus* (Gryczan, In: The Molecular Biology of the *Bacilli*, Academic Press, Inc., NY (1982)), and Streptomyces promoters (Ward et al., *Mol. Gen. Genet.* 203:468–478 (1986)).

Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the encoding sequence. Such ribosome binding sites are disclosed, for example, by Gold et al. (*Ann. Rev. Microbiol.* 35:365–404 (1981)).

Because prokaryotic cells will not produce the EBI3/p35 cytokine with normal eukaryotic glycosylation, expression of the cytokine of the invention by eukaryotic hosts is preferred. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3×63Sg8, and their derivatives. Preferred mammalian host cells include SP2/0 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell, for example in Drosophila larvae. Using insect cells as hosts, the Drosophila alcohol dehydrogenase promoter can be used (Rubin, *Science* 240:1453–1459 (1988)). Alternatively, baculovirus vectors can be engineered to express large amounts of EBI3/p35 in insects cells (Jasny, *Science* 238:1653 (1987); Miller et al., In: *Genetic Engineering* (1986), Setlow, J. K., et al., eds., Plenum, Vol. 8, pp. 277–297).

Any of a series of yeast gene sequence expression systems may also be utilized which incorporate promoter and termination elements from the genes coding for glycolytic enzymes which are produced in large quantities when the yeast are grown in media rich in glucose. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secrete peptides bearing leader sequences (i.e., pre-peptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or which are subject to chemical (such as metabolite) regulation.

As discussed above, expression of EBI3/p35 in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature* (London) 290:304–310 (1981)); the yeast gal4 gene sequence promoter (Johnston et al., *Proc. Natl. Acad. Sci. (USA)* 79:6971–6975 (1982); Silver et al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes EBI3/p35 does not contain any intervening codons which are capable of encoding a methionine (i.e., AUG). The presence of such codons results either in a formation of a fusion protein (if the AUG codon is in the same reading frame as the EBI3 or p35 coding sequence) or a frame-shift mutation (if the AUG codon is not in the same reading frame as the EBI3 or p35 coding sequence).

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may, for example, provide for prototrophy to an auxotrophic host or may confer biocide resistance to, e.g., antibiotics, heavy metals, or the like. The selectable marker gene sequence can either be directly linked to the DNA gene sequences to be expressed, or introduced into the same cell by co-transfection. Additional elements may also be needed for optimal synthesis of EBI3 or p35 mRNA. These elements may include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColEl, pSC 101, pACYC 184, and πVX. Such plasmids are, for example, disclosed by Sambrook, et al. (*Molecular Cloning: A Laboratory Manual*, second edition, edited by Sambrook, Fritsch, & Maniatis, Cold Spring Harbor Laboratory, 1989)). Bacillus plasmids include pC194, pC221, pT127, and the like. Such plasmids are disclosed by Gryczan (In: *The Molecular Biology of the Bacilli*, Academic Press, NY (1982), pp. 307–329). Suitable Streptomyces plasmids include pIJ101 (Kendall et al., *J. Bacteriol.* 169:4177–4183 (1987)), and streptomyces bacteriophages such as φC31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J Bacteriol.* 33:729–742 (1978)).

Preferred eukaryotic plasmids include, for example, BPV, EBV, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980)). Other preferred eukaryotic vectors are viral vectors. For example, and not by way of limitation, the pox virus, herpes virus, adenovirus and various retroviruses may be employed. The viral vectors may include either DNA or RNA viruses to cause expression of the insert DNA or insert RNA. In addition, DNA or RNA encoding the EBI3 and/or p35 polypeptides may be directly injected into cells or may be impelled through cell membranes after being adhered to microparticles (see below).

As noted above, although it is preferred that the nucleic acids encoding the EBI3 protein and the p35 subunit be included in a single dicistronic expression vector, this need not be the case. Rather, two separate expression vectors, one operably encoding the EBI3 protein and the other operably encoding the IL12 p35 subunit, can be constructed using regulatory sequences and vectors as described above. Appropriate host cells may then be co-transformed with these vectors such that both the EBI3 and p35 polypeptides are expressed in the same cell and are capable of associating to form the EBI3/p35 heterodimer. It is also possible to transform one cell or group of cells with a vector operably encoding the EBI3 protein, to transform another cell or group of cells with a vector operably encoding the p35 subunit, to isolate the expressed EBI3 and p35 polypeptides from these cells, and to admix the EBI3 protein and the p35 subunit in an appropriate medium (e.g. cell culture media with or without serum) to allow them to form the EBI3/p35 heterodimer. Nonetheless, in preferred embodiments, the recombinant cells of the present invention are either transformed with a single dicistronic vector operably encoding the EBI3 and p35 polypeptides or with two vectors, one operably encoding the EBI3 protein and the other operably encoding the p35 subunit.

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. After the introduction of the vector, recipient cells are grown in a selective medium, which selects for the growth of vector-containing cells. Expression of the cloned gene sequence(s) results in the production of EBI3/p35. This can take place in the transformed cells as such, or following the induction of these cells to differentiate (for example, by administration of bromodeoxyuracil to neuroblastoma cells or the like).

The selection of control sequences, expression vectors, transformation methods, and the like, are dependent on the type of host cell used to express the gene. As used herein, "cell," "cell line," and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Methods of Diagnosing Pregnancy and Threatened Abortion

Because of the high level of synthesis of EBI3 in the placenta, measuring EBI3 or EBI3/p35 in vivo in serum, urine or uterine secretion obtained from a pregnant or potentially pregnant woman provides an important new test to diagnose an early event in implantation of the developing placenta. Further, measurement of the levels of EBI3 and/or EBI3/p35 in serum or urine would be a useful indicator of threatened abortion, in which case the levels would be expected to fall. Given the presumed importance of foetal rejection in spontaneous abortion and the likely role of EBI3/p35 as a natural defense against maternal rejection of the placenta and foetus, the measurement of EBI3 and/or EBI3/p35 levels should be a physiopathologically significant parameter for spontaneous abortion.

The format of the diagnostic test of the present invention would use antibodies to measure EBI3 and/or EBI3/p35 in serum, urine, or uterine secretions. The antibodies may be generated to EBI3 itself or specifically to the EBI3/p35 heterodimer. Because the p35 subunit is expressed in most tissues of the body, antibodies to p35 alone should not be used (except in a "sandwich" assay as described below). Using the substantially pure protein of the present invention, one of ordinary skill in the art may generate such antibodies without undue experimentation according to methods well known in the art. (See, e.g., Catty, D. (ed.) *Antibodies A Practical Approach*, Vols. I and II, IRL Press, Washington, D.C. (1988); Kennett, R., et al. in *Monoclonal Antibodies, Hybridoma: A New Dimension in Biological Analyses*, Plenum Press, New York (1980); and Campbell, A., "Monoclonal Antibody Technology," in *Laboratory Techniques in Biochemistry and Molecular Biology*, Volume 13 (Burdon, R., et al., eds.), Elsevier, Amsterdam (1984)).

In general, a sample of serum, urine, or uterine secretion may be obtained from a pregnant or potentially pregnant woman and may be contacted with the anti-EBI3 or anti-EBI3/p35 antibodies of the invention. Binding of the antibodies to EBI3 or the EBI3/p35 heterodimer may be detected by any of the standard means known in the art. Antibodies to a first EBI3 or EBI3/p35 epitope may, for example, be immobilized on a substrate, contacted with the sample to allow binding of the antibodies to the epitope, and then washed to remove unbound materials. The presence of bound protein may then be assayed by standard means. Alternatively, the assay may be of the "sandwich" type in which a first set of EBI3 or EBI3/p35 antibodies is first contacted with the sample and then washed, and then labeled antibodies to a second EBI3 or EBI3/p35 epitope are added. Binding of the second set of antibodies indicates the presence of EBI3 or EBI3/p35 bound to the first set. The labels used may be of any variety known in the art (e.g. enzymatic, radioactive, bioluminescent). In the sandwich-type assay, it is permissible that one set of antibodies be specific to the p35 subunit. Other antibody tests, including competitive binding tests, will be apparent to one of ordinary skill in the art.

The term "antibody" (Ab) or "monoclonal antibody" (Mab) as used herein is meant to include intact molecules as well as fragments thereof (such as, for example, Fab and $F(ab')_2$ fragments) which are capable of binding an antigen. Fab and $F(ab')_2$ fragments lack the Fc fragment of intact antibody, clear more rapidly from the circulation, and may have less non-specific tissue binding than an intact antibody. Single chain antibodies, humanized antibodies, and fragments thereof, also are included.

Methods of Treatment and Diagnosis Relating to the EBI3/p35 Cytokine

EBI3/p35 may be administered to patients including, but not limited to, the following: (1) Pregnant or potentially pregnant women with a history of infertility, presumed or possibly due to failure of placental implantation; (2) Transplant recipients at risk for organ rejection or those experiencing organ rejection; (3) Patients with autoimmune diseases, for example, due to NK or cytotoxic T cell hyperactivity such as inflammatory bowel disease, lupus, rheumatoid arthritis, sarcoid, or multiple sclerosis; and (4) Patients with infectious disease for example, as results in hyperactive cytotoxic T cell responses that threaten organ destruction (e.g., tuberculous meningitis in which EBI3/p35 would be useful parenterally, administered into the CSF).

Alternatively, the nucleic acids of the present invention, operably encoding an EBI3/p35 cytokine, may be administered to a patient such that the nucleic acids direct expression of the EBI3/p35 cytokine by the patient's cells (or by transplanted cells placed within the patient). Thus, the nucleic acids of the invention may be used therapeutically in the following ways: (1) Expressed in uterine or placental tissue using expression vectors with constitutive or organ-specific promoters; (2) Expressed in an in vitro fertilized ovum using in vitro injected RNAs or appropriate DNA expression vectors; (3) Expressed in transplanted organs using in vitro (pre-transplant) or in vivo (post-transplant) RNA/DNA injection, infection, or transfection; and (4) Expressed in diseased or normal tissues in patients with autoimmune diseases or autoimmune manifestations of infectious diseases as described above. DNA in expression cassettes could employ constitutive or tissue specific promoters. The latter would enable systemic administration and local organ specific expression.

Administration of EBI3/p35, or nucleic acids encoding EBI3/p35, may be via any suitable route including, oral, or parenteral. When it is only necessary to treat a particular site or organ, such as a placenta, uterus, or transplanted organ, the administration may be localized to the site or organ, for example, by injection to or perfusion of the site.

For therapeutic uses, EBI3/p35 or nucleic acids operably encoding EBI3/p35 may be formulated with a pharmaceutically acceptable carrier as part of a pharmaceutical composition. Such a pharmaceutical composition may include the cytokine or nucleic acids in combination with any standard physiologically and/or pharmaceutically acceptable carriers which are known in the art. The compositions should be sterile and contain a therapeutically effective amount of the cytokine or nucleic acids in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

The pharmaceutical composition of the invention may be in the form of a liposome in which the cytokine or nucleic acids are combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like.

When a therapeutically effective amount of the EBI3/p35 cytokine, or nucleic acids encoding the cytokine, is administered orally, the composition will be in the form of a tablet, capsule, powder, solution or elixir. When administered in tablet form, the pharmaceutical composition of the invention may additionally contain a solid carrier such as a gelatin or an adjuvant. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol.

When a therapeutically effective amount of the EBI3/p35 cytokine, or nucleic acids operably encoding the cytokine, is administered by intravenous, cutaneous or subcutaneous injection, the oligonucleotides will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the active ingredient, an isotonic vehicle such as saline solution, Ringer's solution, dextrose solution, dextrose and sodium chloride solution, lactated Ringer's solution, or another vehicle as known in the art. The pharmaceutical composition of the present invention may also contain stabilizers, preservatives, buffers, antioxidants, or other additives known to those of skill in the art.

In some embodiments, when the target cells are readily accessible, administration of the EBI3/p35 cytokine or nucleic acids is localized to the region of the targeted cells in order to maximize the delivery of the active ingredient and to minimize the amount of the active ingredient needed per treatment. Thus, in one preferred embodiment, administration is by direct injection at or perfusion of the site of the targeted cells, such as a placenta, uterus or transplant organ. Alternatively, the nucleic acids of the invention may be adhered to small particles (e.g., microscopic gold beads) which are impelled through the membranes of the target cells (see, e.g., U.S. Pat. No. 5,149,655).

It is believed that doses of EBI3/p35 protein complex ranging from 1 nanogram/kilogram to 100 milligrams/kilogram, depending upon the mode of administration and the particular condition being treated, will be effective. The preferred range is believed to be between 500 nanograms and 500 micrograms/kilogram. The absolute amount, of course, will depend on a variety of factors including the material selected for administration, whether the administration is in singular or multiple doses, individual patient parameters including age, physical condition, size and weight, and the condition being treated. These factors are well known to those of ordinary skill in the art and can be addressed with no more routine experimentation.

EXPERIMENTAL EXAMPLES

The foregoing description of the invention includes many specific examples which are intended to be illustrative but not limiting of the scope of the invention enabled by the description provided herein. In addition, the following data from experiments conducted during the development of the present invention, are presented as illustrative of the nature and utility of the invention and are not intended to limit its scope.

Materials and Methods

Cell culture. BL30, BL41, Louckes and BJAB are EBV (−) BL lines. The BL41/B95-8 cell line was derived from BL41 by infection with the transforming B95-8 EBV (Calender, et al., (1990) Intl. J. Cancer 46:658–663.). SLA, IB4 and W91 are LCLs generated by EBV transformation of primary human B lymphocytes. P3HR1 is an EBV(+) BL cell line infected with the non-transforming P3HR1 EBV. RHEK-1 is an adenovirus 12/SV40 hybrid virus transformed human keratinocyte line. K562, U937 and HL60 are human myeloid leukemia cell lines with erythroid, monocytic and myeloblastic features respectively. Jurkat and MOLT4 are human T cell leukemia lines. TK143 is a human osteosarcoma line. HeLa is a cervical carcinoma cell line. COS7 is a SV40 transformed monkey kidney cell line. Human peripheral blood mononuclear cells (PBMC) were isolated by ficoll separation of blood (Ficoll-Hypaque; Pharmacia, Vineland, N.J.). Cells were resuspended at $1 \times 10^6$ cells/ml in RPMI medium supplemented with 20% fetal bovine serum, and were divided into parallel cultures grown 72 h with or without 2.5 µg/ml pokeweed mitogen (Sigma, St. Louis, Mo.).

Subtractive hybridization and sequence analysis. A BL41/B95-8 cDNA library was screened using subtracted BL41/B95-8 cDNA probes as previously described (Birkenbach, et al., (1993) J. Virol. 67:2209–2220). Nucleotide and predicted amino acid sequences were compared by the BLAST algorithm (Altschul et al. (1990) J. Mol. Biol. 215(3) :403–410) with known sequences of the National Center for Biotechnology Information databases using the Experimental GENINFO(R) BLAST Network Service, through the Molecular Biology Computer Research Resource of the Dana-Farber Cancer Institute. Multiple sequence alignments were performed by the method of Higgins and Sharp, (1988) Gene 73(1):237–244, using the CLUSTAL program (PCGene, IntelliGenetics, Mountain View, Calif.).

RNA preparation and analysis. Cytoplasmic RNA was isolated from exponentially growing cells by acid phenol/guanidinium isothiocyanate extraction (Birkenbach, et al., (1993) J. Virol. 67:2209–2220). Total cellular RNA was purified from excised human spleen and tonsil, and from post-mortem bone marrow by acid phenol/guanidinium isothiocyanate extraction, followed by reprecipitation in 4M LiCl. Polyadenylated IB4, BL41 and BL41/B95-8 RNA were purified by chromatography on oligodeoxythymidylate cellulose. RNA samples (4–12 μg per lane) were denatured, size fractionated on 0.66M formaldehyde, 1% agarose gels and transferred to charged nylon membranes (GeneScreen Plus; New England Nuclear, Billerica, Mass.). Expression in other human tissues was analyzed using a commercially prepared blot (Multiple Tissue Northern; Clontech, Palo Alto, Calif.) containing 2 μg of polyadenylated heart, brain, placenta, lung, liver, kidney, skeletal muscle and pancreas RNA. The RNA blots were hybridized to $^{32}$P-labeled cDNA probes as previously described (Birkenbach, et al., (1993) J. Virol. 67:2209–2220).

Transfections. The protein coding region of the EBI3 cDNA was cloned into the EcoRi site of the eukaryotic expression vector, pSG5 (Stratagene). An EBI3-FLAG expression vector was constructed which included an in-frame fusion of the EBI3 open reading frame 5' with DNA encoding a kinase site (RRASVG) (SEQ ID NO: 5) and FLAG epitope (DYKDDDDK) (SEQ ID NO: 6), inserted into the EcoRI site of pSG5. The entire open reading frame was sequenced. Plasmid DNA was purified by isopycnic banding on CsCl gradients. Approximately 1 ×10$^7$ target cells were transfected with 40 to 50 μg purified plasmid DNA by electroporation at 200 V, 960 μF in 0.4 cm cuvettes (BioRad, Hercules, Calif.). BJAB cells stably expressing EBI3-FLAG protein were established by cotransfection of the pSG5 EBI3-FLAG construct together with an expression vector carrying the hygromycin resistance gene. Transfectants were selected in 400 μg/ml hygromycin and cloned by limiting dilution.

Immunofluorescence. Tissue samples of placenta or tonsil were frozen in dry ice/isopentane. Tissue sections or cell preparations were fixed 10 min in a 50:50 mixture of acetone:methanol at −20° C. After rehydration, slides were incubated with affinity-purified rabbit EBI3 antiserum diluted in PBS/20% goat serum (1:25 dilution) or normal rabbit serum (NRS)(Sigma) at 1:1250 dilution. Antibody binding was detected with FITC-conjugated goat anti-rabbit antibody at 1:500 dilution (Southern Biotechnology, Birmingham, Ala.), and was visualized using a Reichert Microstar IV fluorescence microscope. Frozen tonsil sections were double-stained using rabbit EBI3 antiserum (1:25 diluted) and anti-CD22 mouse monoclonal antibody (1:50 diluted; Dako, Carpinteria, Calif.). Primary antibody binding was detected using FITC-conjugated goat anti-rabbit, and Texas Red-conjugated goat anti-mouse secondary antibodies. For live cell staining, IB4 or transfected BJAB cells were washed three times with PBS and incubated with rabbit EBI3 antiserum diluted 1:25, or NRS diluted 1:1250 in PBS/20% goat serum. Transfected COS7 cells were dissociated from culture flasks with 1 mM EDTA/PBS, and stained in suspension under identical conditions.

Immunoprecipitation and Western blotting. Cells were metabolically labeled for 18 to 24 h with 50 μCi/ml $^{35}$S-methionine (Trans 35S-label; ICN) in methionine-free RPMI medium supplemented with 10% dialyzed fetal bovine serum. Transfected BJAB or COS7 cells were labeled 24 h after electroporation. Labeled cells were washed in ice-cold PBS and lysed in digitonin lysis buffer (1% digitonin, 10 mM triethanolamine pH 7.5, 150 mM NaCl) or NP40 lysis buffer (1% NP40, 20 mM Tris pH 7.4, 150 mM NaCl, 3% glycerol, 1.5 mM EDTA) containing 1 mg/ml BSA and protease inhibitors (1 mM PMSF, 1 μg/ml leupeptin, 1 μg/ml pepstatin). Lysates were centrifuged for 30 min at 14,000×g and precleared with NRS bound to Protein A-Sepharose (Pharmacia) or normal mouse serum bound to protein G-Sepharose. Cleared extracts were incubated at 0° C. for 1 h with primary antibodies. Immune complexes were bound to Sepharose beads and washed with lysis buffer.

In pulse-chase experiments, 1.5×10$^7$ EBI3-Flag stably transfected BJAB cells were preincubated for 1.5 h at 37° C. in 20 ml of Met/Cys free RPMI 1640 medium supplemented with 10% dialysed bovine serum (ICN), and pulsed for 10 min at 37° C. in the same medium containing 2 mCi of $^{35}$SMet/Cys (ICN). Cells were then spun and diluted at a concentration of 10$^6$ per ml in regular RPMI 1640 medium supplemented with 10% bovine serum. At various times, aliquots of 3×10$^7$ cells were harvested, washed in cold PBS, and lysed in 1% NP40 lysis buffer. Cell lysates were immunoprecipitated with anti-Flag M2 antibody (International Biotechnologies, Inc., New Haven, Conn.) as described above. For N-glycanase digestion, immunoprecipitates were washed once in digitonin buffer containing 1 mg/ml BSA, four times in digitonin buffer, twice in 0.5M LiCl, 0.1M Tris pH 7.4, and once in 10 mM Tris, pH 7.4. Immune complexes were eluted from protein A Sepharose by boiling for 5 minutes in 100 μL 50 mM Tris, pH 7.4, 0.5% SDS, 50 mM β-mercaptoethanol. Aliquots (20 μL) of immunoprecipitates were adjusted to 1.25% NP40 and incubated with or without 0.3 units N-glycanase (Genzyme, Boston, Mass.) for 18 hr at 37° C. Samples were boiled in SDS protein sample buffer and analyzed on 10% polyacrylamide gels. Immunoblotting was done using standard techniques (Birkenbach, et al., (1989) J. Virol. 63:4079–4084).

Purification and amino acid sequencing of EBI3-associated proteins. BJAB cells stably transfected with an EBI3-Flag expression vector were washed in cold PBS, lysed by adding ice-cold 1% NP40 lysis buffer (1 ml/10$^8$ cells) containing 150 mM NaCl, 50 mM Tris pH 7.4, 1.5 mM EDTA, 3% glycerol, 1 mM PMSF, 1 μg/ml pepstatin, 1 μg/ml leupeptin, and rocked for 30 min at 4° C. After centrifugation at 14,000×g for 30 min the supernatant was rocked with anti-Flag M2 beads for 1.5 h at 4° C. Beads were washed first with 1% NP40 lysis buffer and subsequently with TBS (10 mM Tris pH 7.4, 150 mM NaCl), and bound proteins were eluted by addition of Flag peptide (250 nM in TBS). After concentration using Centricon 10 (Amicon), proteins were separated by 6.5% SDS-PAGE under reducing conditions and transferred to ProBlott sequencing membrane (Applied Biosystems). Proteins were stained with Ponceau S and bands corresponding to p95 and p60 were excised. In situ digestion with trypsin, peptide analysis by High Performance Liquid Chromatography, laser desorption mass spectroscopy, and Edman microsequencing were performed at the Harvard Microsequencing Facility.

Cloning of cDNA for novel EBV-induced cytokine receptor, EBI3. Two of 25 cDNA clones derived from screening of a BL41/B95-8 cDNA library with a probe depleted for uninfected BL41 cell RNA are cDNA from a novel gene designated EBV-induced gene 3 (EBI3). The complete sequence of the 1161 nucleotide (nt) EBI3 cDNA is shown in SEQ ID NO: 1. A unique AUG codon at nt 14–16 conforms to a Kozak consensus sequence for translational initiation (Kozak (1991) *J. Biol. Chem.* 266:19867–19870) and precedes a 687 nt open reading frame predicted to encode a 25,391 Dalton polypeptide. The first 20 amino acids are highly hydrophobic and are predicted to be a cleavable signal peptide. Two potential N-linked glycosylation sites are also present. The predicted protein shows structural features characteristic of members of the haematopoietin (cytokine) receptor family (Bazan (1990) *Proc. Natl. Acad. Sci.* (*USA*) 87:6934; Cosman (1993) *Cytokine* 5:95). These include 2 pairs of conserved cysteines at positions 35, 46, 79 and 89 and a LSDWS (SEQ ID NO: 7) motif at residues 215 to 219, similar to the WSXWS (SEQ ID NO 8) consensus sequence. Among members of the family, EBI3 is most closely homologous to the receptor for ciliary neurotrophic factor (CNTFR) (30% identity) and to the IL12 p40 subunit (27% identity), with conservative amino acid substitutions at many of the non-identical residues. EBI3 further resembles IL12 p40 mRNA in having a 3' untranslated Alu repeat sequence (Gubler et al. (1991) *Proc. Natl. Acad. Sci* (*USA*) 88:4143'4147; Wolf et al. (1991) *J. Immunol.* 146:3074–3130). Also similar to IL12 p40 and different from other members of this family, EBI3 lacks obvious membrane anchoring sequences such as a hydrophobic or amphipathic segment or a GPI linkage consensus site. Sequencing of five additional clones isolated from the unamplified cDNA library failed to reveal alternative C-terminal domains which could convey membrane association. The murine homologue of EBI3 has been isolated and similarly lacks a transmembrane domain.

EBI3 is expressed in EBV-infected lymphocytes and placenta. Hybridization of $^{32}$P-labeled EBI3 probe to RNA blots detected a 1.4 kb message in the EBV-infected cell lines IB4 and BL41/B95-8. EB13 RNA was undetectable in the EBV(-) control cell line BL41, while parallel blots hybridized with probes for glyceraldehyde phosphate dehydrogenase (GAPDH) and actin demonstrated that the BL41 lane contains as much or more RNA than the EBV-infected cell lanes. Densitometric quantitation of autoradiograph band intensities indicates that BL41/B95-8 and IB4 cells contain at least 200-fold more EBI3 RNA, relative to actin RNA levels, than do BL41 cells. EBI3 is expressed at high levels in two other EBV-transformed LCLs, W91 and SLA, but is undetectable in the EBV-negative BL cell line, BL30, in two T cell lines, MOLT-4 and Jurkat, and in the myelocytic cell lines, U937 or HL60. EBI3 RNA is detected at low levels in the non-transforming EBV mutant BL cell line, P3HR1, in the EBV(-) B cell line, Louckes, and several non-lymphoid cell lines, including K562, TK143, RHEK-1 and HeLa.

A series of EBV-negative BJAB cell lines stably transfected with different EBV latent genes was analyzed. Expression of EBNA-2 or EBNA-3C failed to induce higher EBI3 mRNA expression relative to parental BJAB, or vector-transfected BJAB/neo or BJAB/gpt control cell lines. However, cells converted to expression of the EBV latent membrane protein 1 (LMP-1) had high levels of EBI3 mRNA, comparable to the level in EBV-transformed LCLs or EBV-infected BL41/B95-8 cells. Similar analyses of a series of transfectants in EBV-negative BL41 and Louckes cells also showed induction of EBI-3 gene expression by LMP-1.

In human lymphoid tissues, EBI3 RNA is present at low levels in normal unfractionated cells of tonsil and at significantly higher levels in spleen, but is undetectable in bone marrow and in resting peripheral blood mononuclear cells (PBMC). However, EBI-3 mRNA is induced in PBMC by stimulation with the B and T lymphocyte activating agent, pokeweed mitogen (PWM).

In placenta EBI3 RNA levels were significantly higher than in lymphoid cells. EBI3 RNA was faintly detectable in liver, but immunoglobulin mu heavy chain RNA could also be detected in this tissue indicating infiltration of the liver with B lymphocytes (Birkenbach et al. (1993) *J. Virol.* 67:2209–2220).

Tissue expression of EBI3 was further analysed by immunostaining with polyclonal antiserum. Staining of frozen tissue sections of human placenta demonstrated EBI3 in trophoblast cells lining placental villi with a diffuse cytoplasmic staining and perinuclear accentuation. Expression of EBI3 by trophoblasts has been confirmed by in situ hybridization with an EBI3 anti-sense RNA probe. In human tonsil, EBI3 was detected in scattered mononuclear cells of interfollicular zones. The EBI3-positive cells showed a reticular cytoplasmic staining pattern and have abundant cytoplasm, and indented nuclei which were often larger than nuclei of neighboring lymphocytes. Two color immunofluorescence with rabbit EBI3 antiserum and the mouse monoclonal antibody anti-CD22 indicated that EBI3-positive cells fail to express the B cell marker, CD22. The morphology and location of EBI3-producing cells suggest these may be macrophages. In human spleen, EBI3 positive cells were in perifollicular zones of periarteriolar sheaths and of lymphoid follicles, associated with sinusoids. Overall, EBI3-positive cells were significantly more abundant in spleen than in tonsil, consistent with the northern analysis.

EBI3 is present in the cytoplasm and on the plasma membranes of producing cells. Live IB4 cells, or BJAB cells and COS7 cells transfected with a SV40 promoter EBI3 cDNA expression vector were stained in suspension using rabbit polyclonal EBI3 antiserum. In IB4 lymphocytes, faint membrane fluorescence was observed. More intense plasma membrane staining was observed in both BJAB B lymphocytes and COS7 cells transfected with EBI3 cDNA. An identical pattern was observed in EBI3-Flag transfected BJAB or COS7 cells stained with the anti-Flag M2 monoclonal antibody. Fluorescence staining of live pSG5 vector transfected control cells was not detected with EBI3 antiserum or anti-Flag M2 antibody. Staining of IB4 or of EBI3-transfected BJAB or COS7 cells was not observed using NRS.

Immunostaining of fixed IB4 cells or EBI3-transfected BJAB or COS7 cells revealed cytoplasmic fluorescence in a reticular pattern and weaker plasma membrane staining. No staining was observed in vector control transfected cells or with NRS. The more intense cytoplasmic staining indicates that most cell-associated EBI3 protein is retained in intracytoplasmic compartments.

EBI3 is a secreted glycoprotein. EBI3 antiserum identified a 33 kD protein in immunoblots of placenta and of EBV(+) BL41/B95-8 and IB4 cells, but not in EBV(-) BL41 cells. A protein of identical size was detected in lysates of BJAB or COS7 cells transfected with EBI3 cDNA pSG5 expression vector, but was not present in control COS7 or BJAB cells transfected with the pSG5 expression vector alone. These results confirm that the EBI3 cDNA contains the complete reading frame. In addition to the predominant 33 kD protein, 30 kD and 24–25 kD proteins were also detected in EBI3-transfected BJAB and COS7 cells. These are probably stable degradation products as they are not observed with short times of pulse labeling and immunoprecipitation.

To determine how much of the 33 kDa apparent size of EBI3 is due to N-glycosylation, $^{35}$S-labeled EBI3 was immunoprecipitated from IB4 cell lysates and incubated in vitro with N-glycanase to remove unprocessed as well as Golgi processed N-linked sugars. This reduced the apparent size from 33 kD to 28 kD. Similar quantitative reduction was observed with endoglycosidase H, indicating that most of the cell-associated EBI3 has not been Golgi processed.

Surprisingly, in filtered supernatants from transiently transfected COS7 or BJAB cells, EBI3 is 34 kD, slightly larger than cell-associated EBI3. As expected, no reactivity was detected in supernatants of pSG5 vector transfected control cells.

Similar findings were obtained with immunoprecipitated $^{35}$S-methionine-labeled, transiently transfected BJAB or COS7 cells. A 34 kD protein was specifically precipitated which was not detected in immunoprecipitates of pSG5 vector transfected control BJAB or COS7 cell supernatants, or in supernatants precipitated with serum from non-immunized rabbits. As previously observed in immunoblots, the secreted protein is slightly larger than the protein from cell lysates.

EBI3 associates with calnexin and a 60 kD protein. Proteins of 95 kD and 60 kD co-immunoprecipitated with EBI3 from digitonin or NP40 lysates of $^{35}$S-methionine-labeled BJAB cells transfected with EBI3-Flag or EBI3. Proteins of identical size were detected in anti-Flag M2 immunoprecipitates from EBI3:FLAG-transfected COS7 cells, and in EBI3-immunoprecipitates from EBI3-transfected COS7 cells. The 95 and 60 kD proteins were not precipitated with the M2 Mab or EBI3 Ab from vector transfected control BJAB or COS7 cells. The 95 kD protein was also observed in immunoprecipitates from IB4 cells with EBI3 specific antiserum. The 95 kD protein was not substantially affected when immunoprecipitates were resolved in non-reducing conditions indicating that the 95 kD protein is not covalently associated with EBI3 by disulfide linkage. In pulse-chase experiments p95 and p60 associated with EBI3 within 10 min. A protein of 78 kD also associated with nascent EBI3. However this association was transient.

To identify p95 and p60, both proteins were purified by immunoaffinity from BJAB cells stably transfected with EBI3:Flag, separated by SDS/PAGE, and protease digested. Sequences for two peptides were obtained for each protein. The two p95 peptides precisely matched peptide sequences from human calnexin, aa 42 to 60 and 163 to 173 respectively (David et al. (1993) J. Biol. Chem. 268:9585–9592). Calnexin is an ER resident molecular chaperone known to associate transiently with many glycoproteins during their transport through the endoplasmic reticulum (David (1993) supra; Bergeron et al. (1994) TIBS 19:124–128). Staining of fixed, transiently EBI3-transfected BJAB cells with anti-calnexin antibody (Mab AF8; Hochstenbach et al. (1992) Proc. Natl. Acad. Sci. (USA) 89:4734–4738) confirmed pan-cytoplasmic expression. While live cell immunostaining of these cells demonstrated membrane EBI3 expression, no membrane staining with calnexin antibody was detected, indicating that calnexin accounts for EBI3 localization in the endoplasmic reticulum, but does not account for EBI3 association with the plasma membrane.

For p60, the two peptide sequences were not identical to any sequences in the data bases. A degenerate oligonucleotide probe complementary to the RNA sequence predicted to encode a portion of the first peptide was used to isolate p60 cDNA clones from the BL41/B95-8 cDNA library. The predicted protein encoded by the p60 clones contains regions which match identically both peptide fragments, and has limited homology to the Drosophila Ref 2(P) protein (Dezelee et al. (1989) EMBO J. 8:3437–3446). However, no potential signal peptide for membrane translocation or transmembrane domain was identified. These results indicate that p60 is a cytoplasmic protein which may associate with EBI3 via the cytosolic domain of calnexin or some other, as yet unidentified EBI3-associated integral membrane protein.

The p35 subunit of IL12 associates in vivo with EBI3 to form a soluble non-covalent heterodimer. To investigate the in vivo association between EBI3 and p35, coimmunoprecipitation experiments were performed in an EBV (−) B lymphoblast cell line (BJAB) transiently expressing EBI3 and a carboxyterminal FLAG-tagged p35, or an unrelated cytoplasmic FLAG-tagged control protein (FLAGLMP1CT). BJAB cells were electroporated with pSG5 vector expressing the proteins indicated by a plus at the top of FIG. 1. Digitonin lysates obtained 24 hours post-transfection or culture supernatants collected 48 hours post-transfection were subjected to immunoprecipitation with anti-FLAG M2 monoclonal antibody followed by protein G (FIG. 1A, lanes 6–10) or anti-FLAG M2 affinity gel (FIG. 1B, lanes 6–10). Ten percent of the total cell lysates (FIG. 1A, lanes 1–5), 2.5% of the total cell culture supernatants (FIG. 1B, lanes 1–5) and immunoprecipitates (FIG. 1A and B, lanes 6–10) were analyzed by SDS-PAGE on a 10% gel in reducing conditions and subjected to western blot analysis using affinity-purified rabbit EBI3 antiserum followed by chemiluminescent detection. The positions of the molecular weight markers (in kilodaltons) are shown on the left of FIGS. 1A and 1B. Several EBI3 bands ranging from 27 to 33 kD were observed in anti-FLAG immunoprecipitates from cells coexpressing EBI3 and p35FLAG (FIG. 1A, lane 9) but not in anti-FLAG immunoprecipitates from cells expressing EBI3 or p35FLAG alone (lanes 6–8), or coexpressing EBI3 with the FLAG-tagged control protein (lane 10). Similar coimmunoprecipitation experiments performed from cell culture supernatants showed that a significant fraction of secreted EBI3 coprecipitated with p35FLAG (FIG. 1B, lane 9). No signal was detected in anti-FLAG immunoprecipitates from the cell culture supernatant of BJAB cells coexpressing EBI3 with a secreted FLAG-tagged control protein, i.e. p40FLAG (data not shown).

To confirm these findings, the reverse coimmunoprecipitation experiments were performed. COS cells were transiently transfected with a pSG5 p35 expression vector together with an EBI3FLAG or EBI3 expression vector as indicated at the top of FIGS. 2A and 2B, and lysed 48 hours post-transfection in 0.5% NP40 lysis buffer. Cell lysates were submitted to immunoprecipitation with anti-FLAG M2 monoclonal antibody (FIG. 2A) or with affinity-purified EBI3 antiserum (FIG. 2B). Ten percent of the total cell lysates obtained before immunoprecipitation and immunoprecipitated material were analyzed on a 10% gel in reducing conditions and subjected to immunoblot analysis using IL12 polyclonal antisera (FIGS. 2A and B, top panels) or EBI3 polyclonal antisera (FIGS. 2A and B, bottom panels) followed by chemiluminescent detection. The positions of the molecular weight markers (in kilodaltons) are shown on the left of each panel. A major band of 33 kDa corresponding to p35 was observed in anti-FLAG or anti-EBI3 immunoprecipitates from COS cells expressing p35 together with EBI3FLAG or EBI3 (FIG. 2A upper panel, lane 9 and FIG. 2B upper panel, lane 8, respectively), but not in the control immunoprecipitates. Similar results were observed in anti-FLAG immunoprecipitates from cell culture supernatants (data not shown). Thus, EBI3 specifically associates with p35 to form a novel soluble heterodimeric cytokine, EBI3/p35. Coimmunoprecipitation experiments performed in non-reducing conditions showed the association is not covalent (data not shown).

Figure 3:
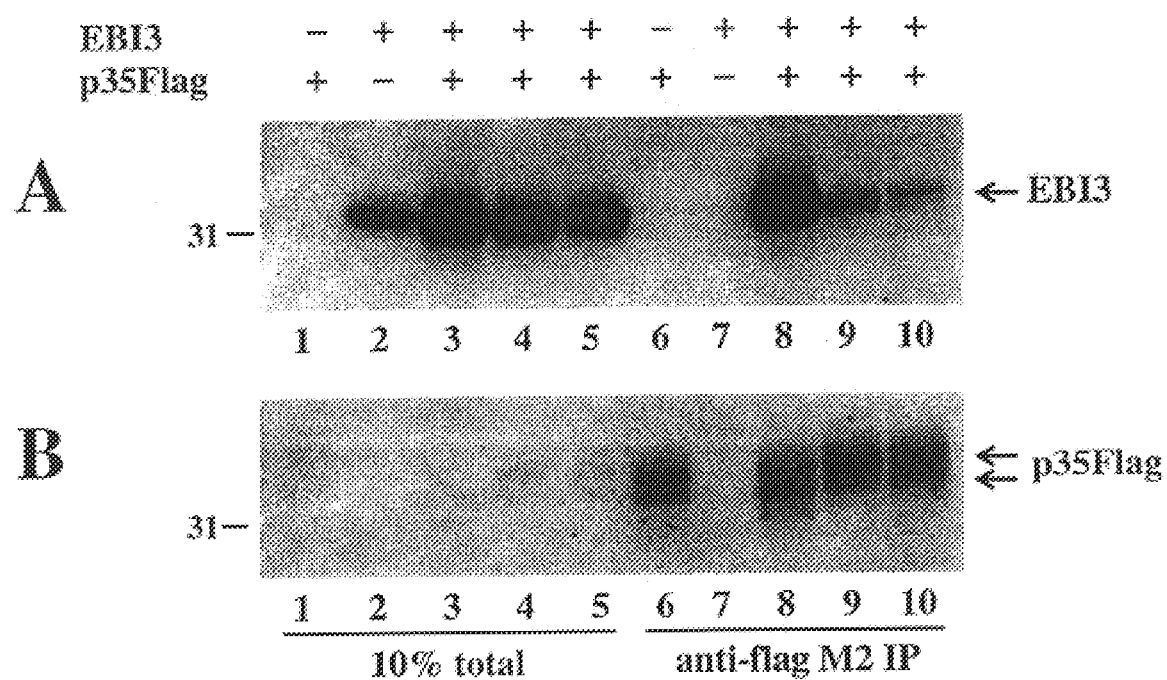
FIG. 3 contains computer digitized images of chemiluminescent immunoblots demonstrating that p35 and EBI3 can associate in solution as detected by EBI3 antiserum (FIG. 3A) or IL12 antiserum (FIG. 3B).

EBI3 and p35 can associate in solution. We next investigated whether EBI3 and p35 non-covalent association requires intracellular association or can take place in solution. To this end, COS cells were electroporated with EBI3 and p35FLAG expression vectors as indicated at the top of FIG. 3. COS cells were either cotransfected with EBI3 and p35FLAG expression vectors (lanes 3 and 8), or were independently transfected with EBI3 or p35FLAG expression vectors and then cocultivated (lanes 4–5, 9–10). After 48 hours (lanes 1, 2, 6, and 7) or 65 hours of culture (lanes 3–5, 8–10), cell culture supernatants were harvested and submitted to immunoprecipitation with anti-FLAG M2 affinity gel. Immunoprecipitates were separated on an 11% SDS-PAGE gel in reducing conditions, and subjected to western blot analysis using EBI3 antisera (FIG. 3A) or IL12 antisera (FIG. 3B) followed by chemiluminescent detection. The positions of molecular weight markers are indicated on the left of FIGS. 3A and B, and the positions of EBI3 and p35 are shown by arrows. In 10 both cases, EBI3 coimmunoprecipitated along with p35FLAG. Thus, EBI3/p35 association does not require intracellular coexpression of both proteins.

Figure 4:
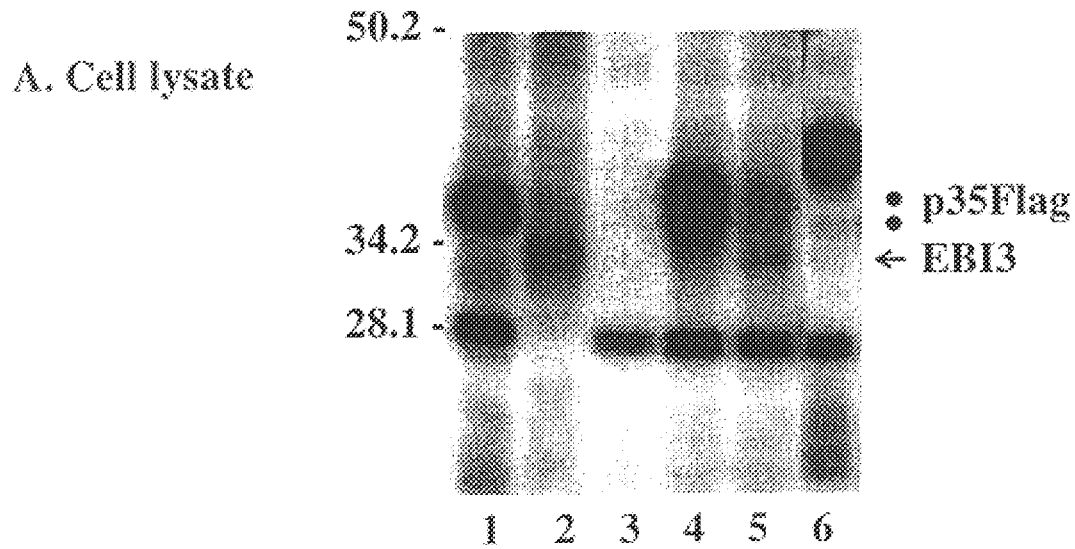
FIG. 4 contains computer digitized images of immunoprecipitates of radioactively labeled proteins showing the effect of EBI3 coexpression on p35 secretion in cell lysates (FIG. 4A) or cell culture supernatants (FIG. 4B) of BJAB cells.
Figure 4:
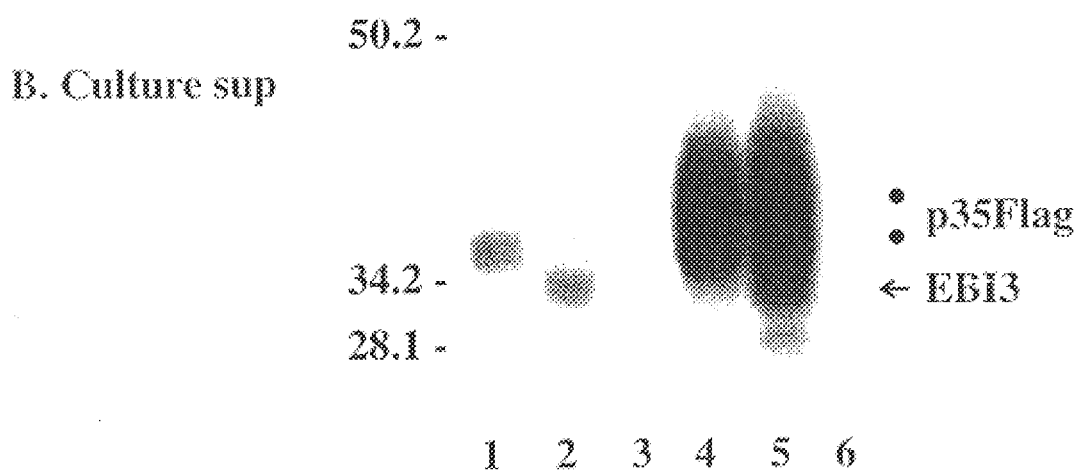

Effect of EBI3 and p35 coexpression on their secretion. Both the p35 subunit of IL-12 and EBI3 have been reported to be not efficiently secreted when expressed alone in cells, EBI3 accumulating in the endoplasmic reticulum associated with calnexin. Immunoblot analysis performed in transiently transfected COS cells (see above, FIG. 2) or BJAB cells (data not shown) showed a lower amount of total cellular p35 when EBI3 was coexpressed, suggesting that EBI3 coexpression may facilitate p35 secretion. However, the low sensitivity of p35 immunoblotting reagents did not allow detection of p35 level in the cell culture supernatants in these experiments. To further investigate whether EBI3 coexpression increases p35 secretion, coimmunoprecipitation experiments were performed in BJAB cells labelled with $^{35}$S-Met/Cys. BJAB cells were electroporated with pSG5 vectors expressing the proteins indicated at the top of FIG. 4. Approximately 22 hours post-transfection, cells were labelled with $^{35}$S-Met/Cys for 18 hours. 0.5% NP40 solubilized cell extracts (FIG. 4A) or cell culture supernatants (FIG. 4B) were subjected to immunoprecipitation with anti-FLAG M2 antibody (FIG. 4A, lanes 1, 3–6), anti-FLAG M2 affinity gel (FIG. 4B, lanes 1, 3–6) or with affinity-purified rabbit EBI3 antiserum (FIGS. 4A and B, lane 2) and the immunoprecipitates separated on a 10% SDS-PAGE gel in reducing conditions. Numbers at the left of FIGS. 4A and B indicate the position of protein molecular weight standards (in kilodaltons). The positions of EBI3 and p35 are indicated on the right of FIGS. 4A and B. As expected from the immunoblot analysis, a protein comigrating with EBI3 was observed in anti-FLAG immunoprecipitates from cell lysate or cell culture supernatants of BJAB cells coexpressing EBI3 and p35FLAG (lanes 5), but not in anti-FLAG immunoprecipitates from cell lysate or culture supernatants from BJAB cells expressing EBI3 or p35FLAG alone (lanes 3 and 4), or coexpressing EBI3 with a FLAG-tagged control protein (lanes 6). The amount of EBI3 associated with p35 is underestimated by the higher content of methionine and cysteine in p35 compared to that of EBI3. Interestingly, a higher ratio of secreted as compared to intracellular form of p35FLAG was observed when EBI3 was coexpressed (secondary immunoprecipitation from the cell culture supernatant showed no significant p35FLAG immunoprecipitation, indicating that the amount of FLAG antibody was not limiting, data not shown). Thus, coexpression of EBI3 results in enhanced p35 secretion.

Figure 2:
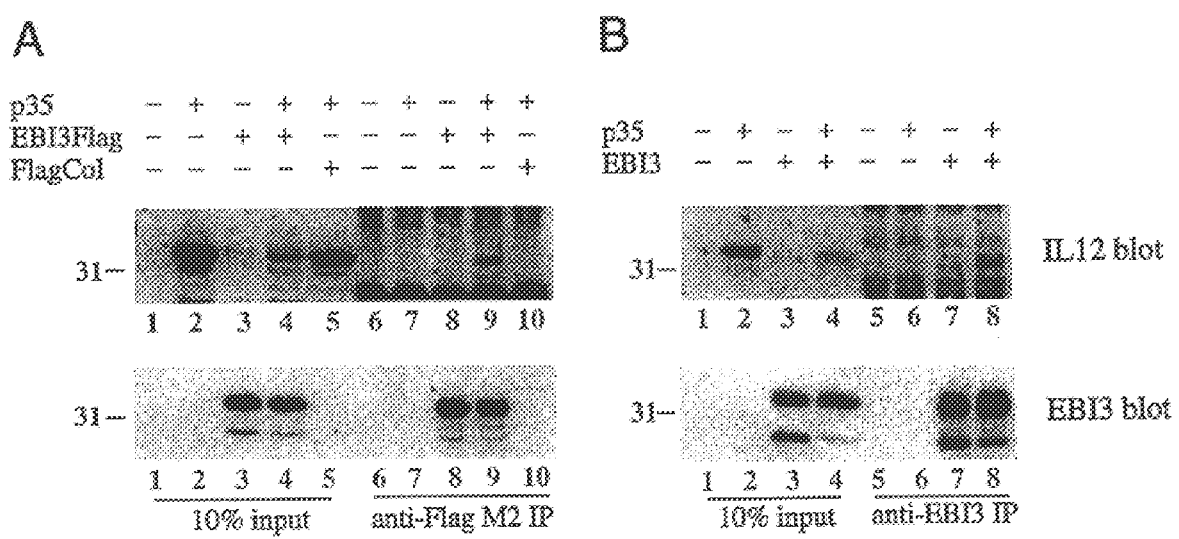
FIG. 2 contains computer digitized images of chemiluminescent immunoblots showing that p35 associates with EBI3FLAG (FIG. 2A) or EBI3 (FIG. 2B).
Figure 5:
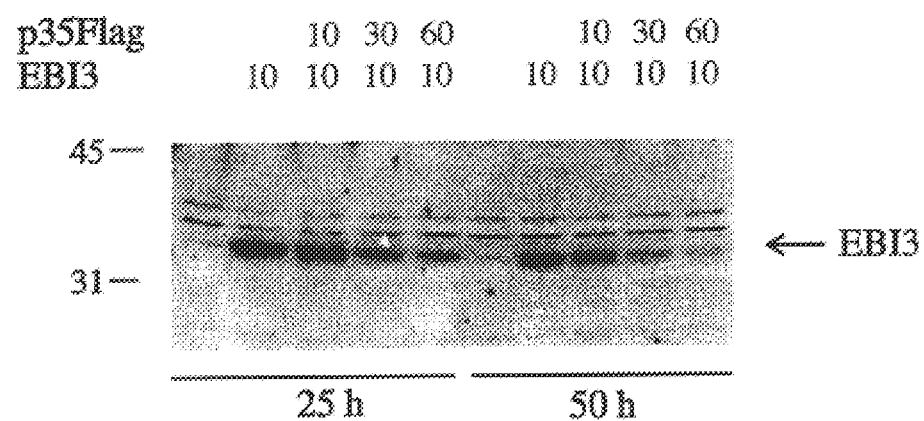
FIG. 5 contains a computer digitized image of a chemiluminescent immunoblot showing the effect of p35 coexpression on EBI3 biosynthesis.

Transient cotransfection of equivalent amounts of EBI3 and p35 expression vectors did not result in a decreased amount of intracellular EBI3 (see above, FIGS. 1 and 2). To determine the effect of increasing amounts of p35 expression on EBI3 secretion, BJAB cells ($10^7$ per transfection) were transiently transfected with a low amount of EBI3 expression vector (10 μg) together with an increasing amount of p35FLAG expression vector (10–60 μg) as indicated at the top of FIG. 5. In all transfections, the total amount of DNA transfected was maintained constant by addition of empty pSG5 vector. After 25 or 50 hours, the cells were lysed in 1% NP40 lysis buffer, cell lysates from 1.5×$10^6$ cells were analyzed by SDS-PAGE on a 10% gel, and subjected to immunoblot analysis using EBI3 antisera. The positions of molecular weight markers (in kilodaltons) are shown on the left of FIG. 5. An increasing ratio of secreted vs intracellular form of EBI3 was observed in immunoblots with increasing p35 expression, suggesting that p35 coexpression may facilitate EBI3 secretion (FIG. 5 and data not shown). The reciprocal effect of EBI3 and p35 on their secretion suggests the two subunits are natural partners.

We claim:

1. A substantially pure EBI3/p35 protein comprising a complex of
   a first polypeptide comprising a p35 subunit of IL12; and
   a second polypeptide comprising an EBI3 protein.

2. The substantially pure EBI3/p35 protein as in claim 1 wherein said EBI3/p35 protein comprises a polypeptide having the amino acid sequence of SEQ ID NO: 2.

3. The substantially pure EBI3/p35 protein as in claim 1 wherein said first polypeptide and said second polypeptide are fused.

4. A preparation comprising a sterile formulation of the substantially pure EBI3/p35 protein of claims 1, 2 or 3 and a pharmaceutically acceptable carrier.

5. A substantially pure EBI3/p35 protein complex encoded by one or more isolated nucleic acids selected from the group consisting of (1) isolated nucleic acids comprising a first expression vector including a first expression cassette and a second expression vector including a second expression cassette, and (2) an isolated nucleic acid comprising an expression vector including a first expression cassette and a second expression cassette, wherein in (1) and (2), the first expression cassette operably encodes a p35 subunit of IL12 and the second expression cassette operably encodes an EBI3 protein.

6. The substantially pure EBI3/p35 protein complex of claim 5, wherein the second expression cassette comprises a nucleic acid selected from the group consisting of
   (a) a complete coding region of SEQ ID NO: 1;
   (b) nucleic acids which hybridize under stringent hybridization conditions to the complement of the nucleic acid of (a) and which code for EBI3 protein; and
   (c) nucleic acids that differ from the nucleic acids of (a) and (b) in codon sequence due to the degeneracy of the genetic code.

7. The substantially pure EBI3/p35 protein complex of claim 5 wherein the first expression cassette comprises a nucleic acid selected from the group consisting of
   (a) a complete coding region of SEQ ID NO: 3;
   (b) nucleic acids which hybridize under stringent hybridization conditions to the complement of the nucleic acid of (a) and which code for a p35 subunit of IL12; and
   (c) nucleic acids that differ from the nucleic acids of (a) and (b) in codon sequence due to the degeneracy of the genetic code.

8. The substantially pure EBI3/p35 protein complex of claim 6 wherein the first expression cassette comprises a nucleic acid selected from the group consisting of
   (a) a complete coding region of SEQ ID NO: 3;
   (b) nucleic acids which hybridize under stringent hybridization conditions to the complement of the nucleic acid of (a) and which code for a p35 subunit of IL12; and
   (c) nucleic acids that differ from the nucleic acids of (a) and (b) in codon sequence due to the degeneracy of the genetic code.

9. The substantially pure EBI3/p35 protein complex of any one of claims 5, 6, 7 or 8 wherein the coding regions of the first expression cassette and the second expression cassette are constructed and arranged to encode a fusion protein comprising an EBI3 portion and an IL12 p35 subunit portion.

* * * * *